United States Patent [19]

Israel et al.

[11] Patent Number: 5,304,211
[45] Date of Patent: Apr. 19, 1994

[54] APPARATUS FOR ADMINISTERING ELECTRICAL AVERSIVE STIMULUS AND ASSOCIATED METHOD

[75] Inventors: Matthew L. Israel, Newton, Mass.; David Marsh, Harmony, R.I.

[73] Assignee: Behavior Research Institute, Providence, R.I.

[21] Appl. No.: 796,713

[22] Filed: Nov. 25, 1991

[51] Int. Cl.⁵ .......................... A61N 1/08; A61N 1/38
[52] U.S. Cl. ........................ 607/58; 361/232; 908; 607/72
[58] Field of Search .............. 128/903, 419 R, 421, 128/848, 419 S; 361/232; 119/29

[56] References Cited

U.S. PATENT DOCUMENTS

| | | | |
|---|---|---|---|
| 2,800,104 | 7/1957 | Cameron et al. | 119/29 |
| 3,478,344 | 11/1969 | Schwitzgebel et al. | 128/903 |
| 3,589,337 | 6/1971 | Doss | 119/29 |
| 3,868,545 | 2/1975 | Caron | 361/232 |
| 3,885,576 | 5/1975 | Symmes | 361/232 |
| 3,998,209 | 12/1976 | Macvaugh | 128/848 |
| 4,202,293 | 5/1980 | Gonda et al. | 119/29 |
| 4,440,160 | 4/1984 | Fischell et al. | 128/132 R |
| 4,943,885 | 7/1990 | Willoughby et al. | 361/232 |
| 5,054,428 | 10/1991 | Farkus | 119/29 |

OTHER PUBLICATIONS

Webber, "A Simple Battery-Powered Stimulator for Aversion Therapy," Med. & Biol. Eng., vol. 6, pp. 445-446, Feb. 1968.
Ali et al., "Instr. & Techniques: A Self-contained, Regulated, Burst-firing Constant-current AC Shock Gen.," Behav. Research, vol. 9, pp. 326-333, Aug. 1977.
Farrall Instruments, Inc., "Instructions for Whistle Stop Wireless Stimulator," (Grand Island, Nebr., 1978).
Human Technologies, Inc., "SIBIS" (St. Petersburg, Fla. 1989).
T. Linscheid, et al., "Clinical Evaluation of the Self-Injurious Behavior Inhibiting System (SIBIS)," Journal of Applied Behavior Analysis, No. 1 pp. 53-78 (Ann Arbour, Mich. Spring 1990).

Primary Examiner—Kyle L. Howell
Assistant Examiner—Kennedy J. Schaetzle
Attorney, Agent, or Firm—Arnold B. Silverman; George K. Stacey

[57] ABSTRACT

An apparatus for administering electrical aversive stimulus is provided. The apparatus includes a remote transmitter, a receiver/stimulator, and an electrode. The receiver/stimulator is activated by an electromagnetic signal generated by the transmitter. In response, the receiver/stimulator generates an electrical stimulus pulse which is administered to the individual through the electrode. The receiver/stimulator and electrode are worn by the individual. Stimulation indicator means on the receiver/stimulator provides a positive indication that the stimulation has been administered to the individual. Various characteristics of the electrical stimulus pulse may be adjusted to vary the individual's perceived averseness of the stimulus. A method of treatment utilizing the apparatus of this invention is also provided.

32 Claims, 5 Drawing Sheets

APPARATUS FOR ADMINISTERING ELECTRICAL AVERSIVE STIMULUS AND ASSOCIATED METHOD

BACKGROUND OF THE INVENTION

1. Field of the Invention

This invention relates to an apparatus and method for deterring or decelerating undesirable behavior by an individual through the use of aversive stimulus. More specifically, this invention relates to a remotely controlled apparatus for administering electrical aversive stimulus to an individual and a method of treatment using the apparatus.

2. Description of Prior Art

It is well known to use aversive stimulus, such as the application of an electric shock, to deter certain types of undesirable behavior. For example, therapists have used electrical aversive stimulus to deter or decelerate self-injurious behavior in individuals. Electrical aversive stimulation has also been used to educate or train individuals. For example, aversive stimulus has been used to educate or train individual using a method known as "behavior rehersal". Behavior rehersal is typically used on individual who have exhibited undesired behavior in the past. Often, the undesired behavior that the individuals exhibited in the past was extreme, such as exhibiting violence against others. With behavior rehersal, the individual is prompted to engage in a form of the undesired behavior or is vividly reminded of the past undesired behavior. When the individual engages in the behavior or when it is clear that the individual recalls the behavior, aversive stimulus is administered to the individual in order to remind him or her of what will occur if he or she engaged in that type of behavior in the future.

Aversive stimulation has also been used to train animals.

U.S. Pat. No. 4,440,160 discloses an apparatus that may be worn on the body of the individual to be treated. The apparatus is said to automatically sense the types of patient movements associated with self-injurious behavior. In response to those movements, an electrical aversive stimulus is automatically administered.

When aversive stimulus is used to educate or train an individual, such as when behavior rehersal is used, it may be desirable to utilize a stimulus in which the aversiveness, as perceived by the individual being treated, is less than that of a stimulus which is used to deter or decelerate the individual's present behavior.

There remains a need for a compact apparatus for administering aversive stimulus which may be remotely activated by a therapist, and which provides an indication that the stimulus has been administered. There also remains a need for an apparatus which generates a stimulus having various characteristics which may be adjusted in order to vary the aversiveness of the stimulus as perceived by the individual.

In addition, there remains a need for a method of administering aversive stimulus in which the actual administration of the stimulus may be monitored and in which various characteristics of the stimulus may be adjusted in order to vary the relative aversiveness of the stimulus.

SUMMARY OF THE INVENTION

As used herein, the term "patient" primarily refers to an individual to which aversive stimulus is administered in order to deter or decelerate undesired behavior in that individual or to otherwise train or educate that individual. It will be appreciated, however, that a "patient" may be administered aversive stimulus for any other suitable purpose as well.

This invention has met the hereinbefore described needs. It provides a compact, remotely controlled aversive stimulation apparatus and a method of treatment using that apparatus. The apparatus includes a transmitter and a receiver/stimulator. The transmitter is remote from the receiver/stimulator. The transmitter includes switch means for causing the transmitter to generate and emit an electromagnetic signal. The receiver/stimulator, which may be worn by a patient, receives the electromagnetic signal and, in response thereto, generates an electrical stimulus pulse. The electromagnetic signal may be digitally coded and the receiver/stimulator may be provided with decoding means such that the receiver/stimulator will only generate an electrical stimulus pulse in response to a specifically coded signal.

An electrode is electrically connected to the receiver/stimulator and is held in electrical contact with the skin of the patient using electrode harness means. The electrode may be secured to a location on the patient that is remote upon from the location of the receiver/stimulator, such as a limb, for example. The electrical stimulus pulse is received by the electrode and delivered to the skin of the patient, where it is perceived as an unpleasant or painful sensation.

Stimulation indicator means on the receiver/stimulator is activated after the electrical stimulus pulse has passed from the electrode to the patient. The stimulation indicator means positively indicates that the stimulus has been administered.

The receiver/stimulator may be provided with adjusting means for adjusting the parameters of various characteristics of the electrical stimulus pulse in order vary the perceived aversiveness of the stimulus. The characteristics that may be adjustable include, but are not limited to, peak current, duty cycle, pulse repetition frequency, and pulse train duration.

This invention also provide a method of treatment using the apparatus of this invention.

It is an object of this invention to provide an apparatus for administering aversive stimulus to an individual and a method of treating an individual using that apparatus.

It is another object of this invention to provide an apparatus for administering aversive stimulus which may be used to deter or decelerate undesired present behavior and which may also be used with a behavior rehersal method of treatment.

It is an object of this invention to provide a compact apparatus for administering aversive stimulation to a patient that may be easily connected to the individual.

It is another object of this, invention to provide an apparatus for administering electrical aversive stimulus to a patient that utilizes a remote, hand-held transmitter that is easy to use and which permits the therapist to the aversive stimulus while being located a administer substantial distance away from the patient.

It is a further object of this invention to provide an apparatus for administering aversive stimulus to an individual that is activated only by an electromagnetic signal that has been coded so as to reduce the likelihood that stimulus will be administered unintentionally by stray electromagnetic signals or to other patients within range who may be wearing similar apparatus.

It is still another object of this invention to provide an apparatus for administering aversive stimulus to a patient that utilizes an electrode that may be positioned at a location on the patient that is remote from the location of the receiver/stimulator.

It is yet another object of this invention to provide an apparatus for administering aversive stimulus that provides a positive indication to the therapist that stimulus has been administered to the patient.

It is still another object of this invention to provide an apparatus for administering aversive stimulus which permits adjustment of various characteristics of the electrical stimulus pulse to vary the perceived aversiveness of the stimulus.

It is an object of this invention to provide an apparatus for administering aversive stimulus which may be connected to an individual in a manner which is comfortable and which does not unduly restrict the patient's movement during normal activity.

It is yet another object of this invention to provide a method of treating a patient using electrical aversive stimulus which utilizes feedback to the therapist indicating that stimulus has been administered.

It is still another object of this invention to provide a method of treating a patient using electrical aversive stimulus wherein various characteristics of the electrical stimulus pulse may be adjusted in order to vary the perceived averseness of the stimulus.

These and other objects of this invention will be more fully understood from the following description on reference to the illustrations appended hereto.

DESCRIPTION OF THE PREFERRED EMBODIMENT

Referring to FIGS. 1-6, there is shown a preferred embodiment of the apparatus of this invention. The apparatus includes transmitter 2 and receiver/stimulator 4. Electrode 6 is electrically connected to receiver/stimulator 4 through electrical cord 8 to be energized thereby.

Figure 1:
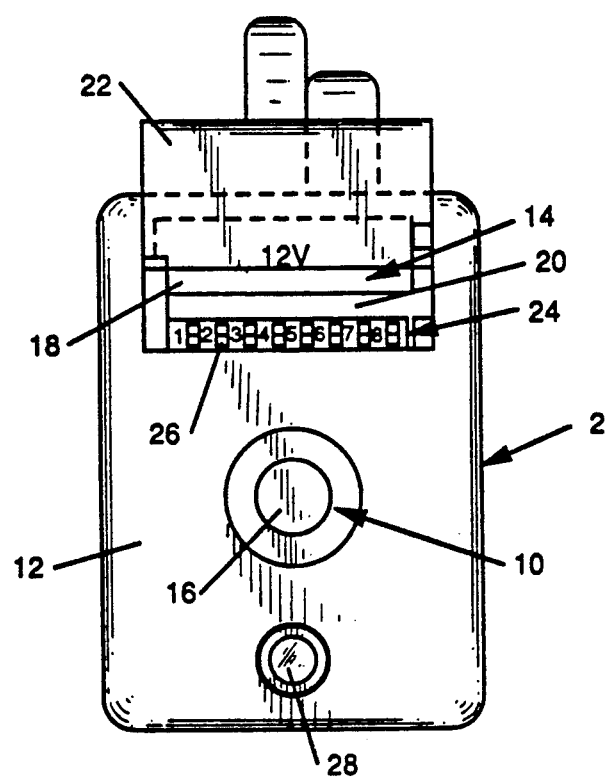
FIG. 1 is a plan view of the transmitter of this invention.
Figure 2:
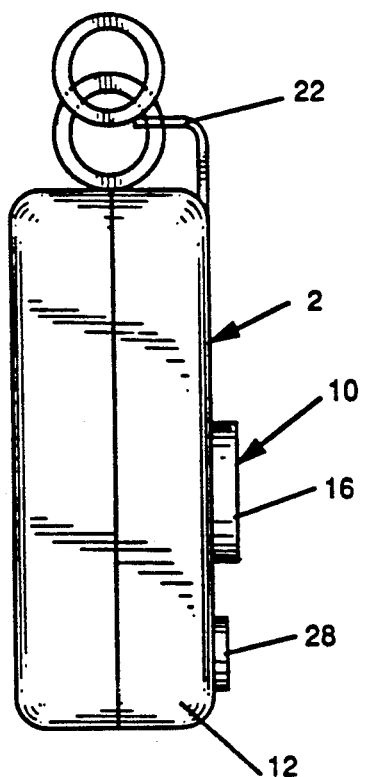
FIG. 2 is a right side elevational view of the transmitter of FIG. 1.
Figure 3:
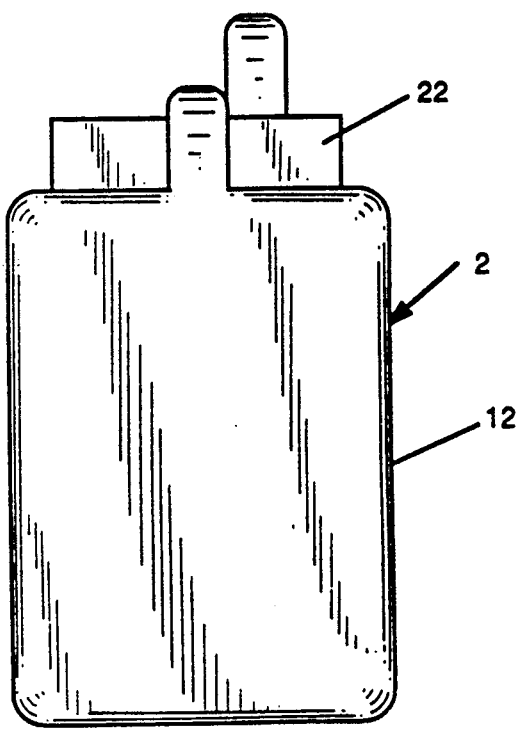
FIG. 3 is a bottom view of the transmitter of FIG. 1.
Figures 4, 5:
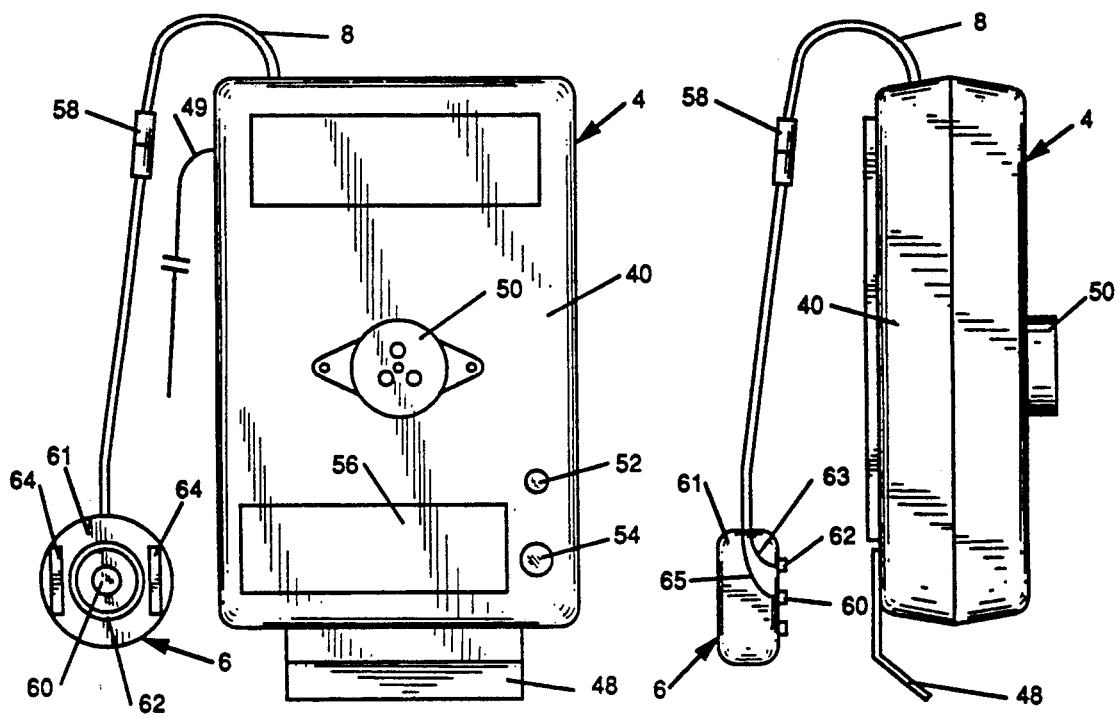
FIG. 4 is a plan view of the receiver/stimulator and electrode of this invention.
FIG. 5 is a right side elevational view of the receiver/stimulator and electrode of FIG. 4.

Referring more particularly to FIGS. 1-3, transmitter 2 generates an electromagnetic signal in a manner well known to those skilled in the art upon the activation of switch means 10. In a preferred embodiment, transmitter 2 includes housing 12, a circuit board (not shown), switch means 10, and power supply 14. Housing 12 is preferably made of plastic polymeric material, but it will be appreciated that any suitable material may be used. Transmitter 2 is preferably of a size such that it will conveniently fit in the user's hand. In a preferred embodiment, switch means 10 consists of spring based transmitter button 16 disposed on the top portion of housing 12. Button 16 is preferably positioned such that a user can easily activate the transmitter while holding the transmitter in his or her hand.

Transmitter power supply 14 is preferably a 12 volt dry cell battery 18. In a preferred embodiment, battery 18 is housed in battery compartment 20 in a portion of transmitter housing 12. A removable battery compartment cover 22 engages transmitter housing 12 to cover battery compartment 20 during normal operation. In FIGS. 1-3, cover 22 is shown as being partially open.

Transmitter 2 may be provided with coding means 24 for digitally coding the electromagnetic signal generated by the transmitter 2. The electromagnetic signal may be coded in a manner well known to those skilled in the art, such as by modulating the signal's pulse width using a binary code, for example. In a preferred embodiment, coding means 24 consists of a bank 26 of from about 8 to 16 dip switches. The setting of the dip switches may be changed to alter the coding of the electromagnetic signal such that only receivers adjusted to respond to the set digital code will be activated by the electromagnetic signal. Such coding will decrease the likelihood that the receiver/stimulator will be activated unintentionally by stray electromagnetic signals. It will also decrease the likelihood that receiver/stimulators worn by other patients who are within the range of the signal will be unintentionally activated.

In a preferred embodiment, transmitter 2 is also provided with a transmitting indicator lamp 28. Indicator lamp 28 becomes illuminated when transmitter 2 is activated, thereby indicating to the user that a signal has been transmitted. Lamp 28 will remain illuminated while button 16 is depressed and go off when button 16 is released.

A suitable transmitter for use with this invention is manufactured by Linear Corporation and sold under the model designation ET2K. However, it will be appreciated that any suitable transmitter may be used.

Referring again to FIGS. 4-6, receiver/stimulator 4 includes housing 40. Enclosed within housing 40 are a receiver circuit board (not shown) and a controller circuit board (not shown). Receiver/stimulator 4 is powered by receiver power supply 42. Receiver power supply 42 preferably consists of two 9 volt batteries 44. In a preferred embodiment, receiver batteries 44 are housed inside receiver battery compartment 46 disposed within housing 40. Receiver battery compartment 46 is preferably provided with a removable battery compartment cover 48. Battery compartment cover 48 is shown as being partially open.

Receiver/stimulator 4 may also be provided with an antenna 49 for receiving the electromagnetic signal generated by transmitter 2. In a preferred embodiment, antenna 49 is a generally flexible, single conductor wire electrically connected to the receiver circuit board. It will be appreciated, however, that any suitable antenna may be used. Antenna 49 may extend outside housing 40.

Receiver/stimulator 4 may also be provided with stimulation indicator means 50. Stimulation indicator means 50 is activated after an electrical stimulus pulse passes between electrode 6 and the patient. Stimulation indicator means 50 is discussed in detail hereinafter.

In a preferred embodiment, receiver/stimulator 4 may be provided with battery test switch 52 and battery test lamp 54. Battery test switch 52 and battery test lamp 54 may be electrically connected with receiver batteries 44 in a manner well known to those skilled in the art to enable the user to test the condition of receiver batteries 44. When battery test switch 52 is activated, if the voltage in receiver batteries 44 is from about 17.5 to 19.5 volts, battery test lamp 54 will become illuminated in green, indicating that the batteries are sufficiently charged. If receiver battery voltage falls below about 17.5 to 3 volts battery test lamp 54 will be illuminated in red, indicating that the batteries should be replaced. In a preferred embodiment, receiver/stimulator 4 will not generate the desired stimulus pulse if the battery voltage falls below about 12 volts. Battery test lamp 54 is preferably a single bulb that may be illuminated in two colors. However, it will be appreciated that any suitable means may be utilized to achieve separate, two color illumination, such as using a separate bulb for each desired color, for example.

Electrode 6 is electrically connected to receiver/stimulator 4 by electrical cord 8. In a preferred embodiment, cord 8 is provided with separable connector 58. Connector 58 may be separated to permit easy replacement of electrode 6. Connector 58 may also be separated to permit cord 8 to be lengthened. Connector 58 may be separated and an extension having connections on the ends thereof which match the separated portions of connector 58 may be inserted between the separated portions of connector 58, thereby increasing the length of cord 8. Inserting an extension into cord 8 allows electrode 6 to be positioned farther away from receiver/stimulator 4 if desired. Lengthening cord 8 also permits the position of electrode 6 on the patient to be changed. Changing the position of electrode 6 on the patient may be desirable when repeated stimulation is required in order that the stimulation is not always administered to the same location on the patient's skin. Such repeated applications of stimulation may result in injury to the skin.

In a preferred embodiment, receiver/stimulator 4 may be provided with information label 56. Information relating to the values of various characteristics of the electrical stimulus pulse generated by that receiver/stimulator may be recorded on label 56 so as to enable a user to select a receiver/stimulator that is set to administer the desired level of aversive stimulation to a particular patient.

Receiver/stimulator housing 40 is preferably made of plastic polymeric material, however, it will be appreciated that any suitable material may be used. Housing 40 is preferably about 4.5 to 6.5 inches long, about 3.5 to 5.0 inches wide, and about 1.29 to 2.5 inches thick. It has been found that this size receiver/stimulator may be conveniently secured to the patient's body in a manner discussed more fully hereinafter, and will not substantially interfere with the patient's comfort or freedom of movement during the patient's normal activities.

In a preferred embodiment, electrode 6 includes a button portion 60 and a ring portion 62. Button portion 60 is preferably disposed within the ring portion of 62. Button portion 60 may have a diameter of about 0.35 to 0.40 inches, but is preferably about 0.375 inches in diameter. Ring portion 62 may have a outer diameter of about 0.85 to 0.900 inches and an inner diameter of about 0.52 to 0.60 inches, with a distance between the outer perimeter and the inner perimeter of the ring being about 0.09 to 0.095 inches. In a preferred embodiment, the outer diameter of ring 62 is about 0.875 inches, the inner diameter is preferably about 0.560, and the distance between the inner perimeter and the outer perimeter of ring 62 is preferably about 0.315 inches. This type of electrode is referred to as a "captured ring" or "Tursky" type electrode. This electrode configuration is preferred because the application of electricity to the patient is confined to a small area of skin between button portion 60 and ring portion 62. Using an electrode of this type also reduces the possibility of the patient receiving transthorasic shock, which may interfere with the patient's normal heartbeat rhythm.

Ring 62 and button 60 of electrode 6 are preferably made of stainless steel. However, it will be appreciated that any suitable electrically conductive material may be used. In a preferred embodiment, ring 62 and button 60 are secured to a base 61. Base 61 is preferably made of substantially rigid material, such as plastic polymeric material or glass, for example. Ring 62 and button 60 may be secured to base 61 using adhesive or any other suitable fastening means known to those skilled in the art. Ring 62 is preferably electrically connected to receiver/stimulator through conductor 63 of electrical cord 8. Button 60 is preferably electrically connected to receiver/stimulator 4 through conductor 65 of electrical cord 8.

Electrode 6 may also be provided with means for securing the electrode in electrical contact with the patient's skin. In a preferred embodiment, slots 64, 66 may be provided to accommodate a strap for holding the electrode in place against a patient's skin, as discussed hereinafter.

Figure 7:
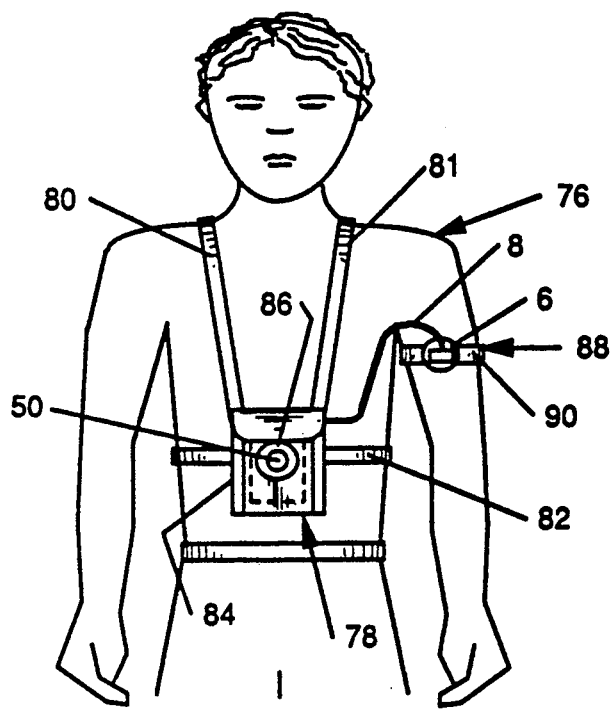
FIG. 7 is a front view showing the apparatus of this invention connected to a patient.
Figure 8:
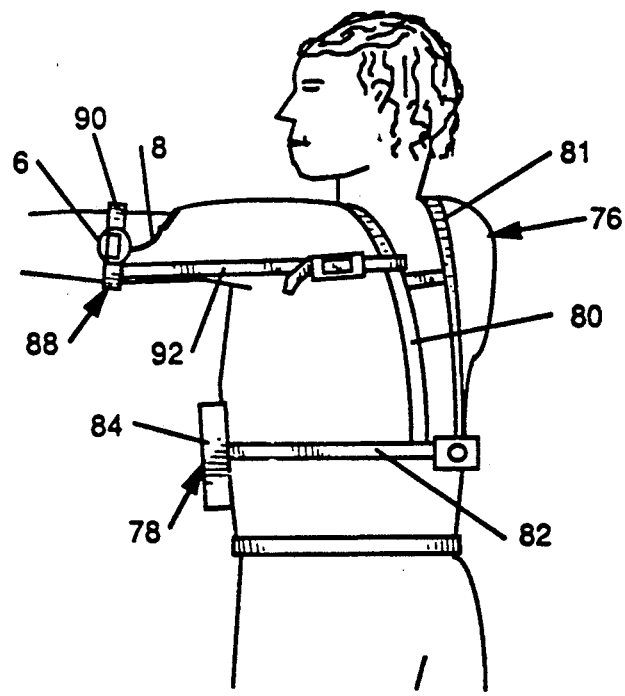
FIG. 8 is a left side elevational view of the patient shown in FIG. 7.

Referring to FIGS. 7 and 8, there is shown a preferred manner of securing receiver/stimulator 4 and electrode 6 to a patient. Patient 76 is fitted with a receiver/stimulator harness 78. Harness 78 preferably has a shoulder straps 80, 81 and belt 82 for holding pocket 84 in place on the front portion of the patient's 76 torso. Receiver/stimulator 4 is preferably received into pocket 84 through the top thereof. Opening 86 in the front portion of pocket 84 may be provided to allow stimulation indicator means 50 to remain exposed. The receiver/stimulator antenna is preferably contained within pocket 84 along with receiver/stimulator 4 during normal operation. In a preferred embodiment, the antenna is not permitted to extend outside pocket 84 during normal operation.

Electrical cord 8 preferably extends outside pocket 84 through the top thereof. Electrode 6 is preferably secured to a portion of the patient's 76 body away from receiver/stimulator 4. Electrode harness means 88 may be provided for holding electrode 6 in place in electrical contact with the skin of the patient 76. In a preferred embodiment, limb belt 90 passes through the slots in the base portion of electrode 6 and across the back thereof and is then secured around a portion of patient's 76 body, such as the upper arm. Strap 92 is preferably secured to one of the straps 80, 81 on apron 78 to further resist slippage of limb belt 90 on patient 76. Straps 80, 81, belt 90 and electrode harness 88 may be made from any suitable material, such as nylon webbing or cotton/elastic blend material, for example. It will be appreciated that any suitable tightening means and buckle means may be used to adjust the length of straps 80, 81, belt 90, and electrode harness 88.

The combination of harness 78 and electrode harness means 88 allows receiver/stimulator 4 and electrode 6 to be easily and comfortably secured to the patient 76 without requiring the use of elastic bandages to hold the units in place. In addition, harness 78 and electrode harness means 88 will not unduly restrict the patient's 76 movement during normal activity.

While use of harness 78 and electrode harness means 88 is a preferred manner for securing receiver/stimulator for an electrode 6 to a patient's body, it will be appreciated that these components may be secured to the patient's body using any suitable means.

Figure 6:
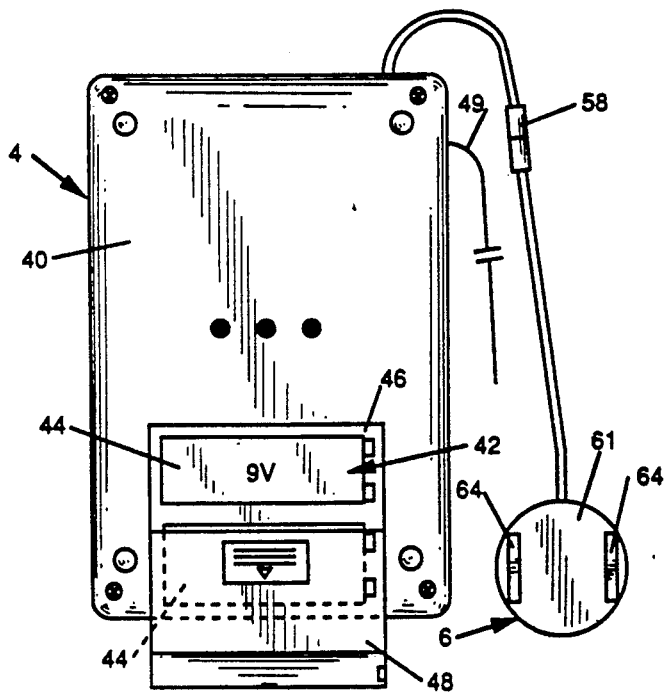
FIG. 6 is a bottom view of the receiver/stimulator and electrode of FIG. 4.
Figure 9:
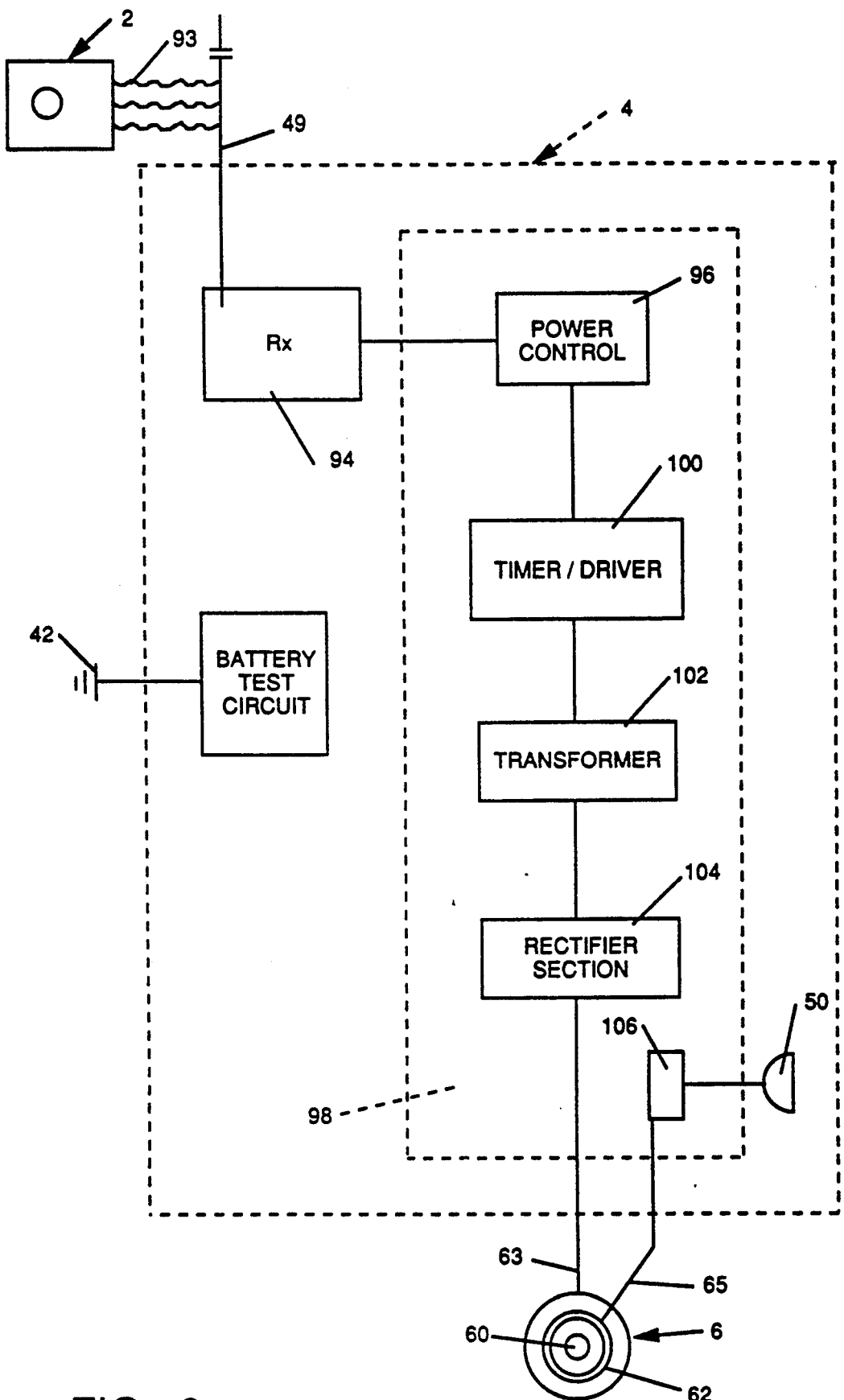
FIG. 9 is a schematic diagram showing details of the receiver/stimulator of this invention.

Referring to FIG. 9, there is shown a schematic diagram of the receiver/stimulator 4 of this invention. Coded electromagnetic signal 93 is generated by transmitter 2. Receiver board 94 is provided with decoding means which may be adjusted so that receiver board 90 will only recognize an electromagnetic signal emitted by a transmitter having the proper digital code. The decoding means of receiver board 94 may be a series of about 8 to 16 dip switches substantially similar to the dip switches 26 located on transmitter 2, as shown in FIG. 1. It will be appreciated, however, that any suitable decoding means may be used. When dip switches are used, they may be disposed within housing 40 of receiver/stimulator 4, as shown in FIG. 6.

Referring again to FIG. 9, when the properly coded electromagnetic signal is received by antenna 49, power control section 96 of controller board 98 is activated. Power control section 96 turns on the power to the rest of receiver/stimulator 4. Power to the receiver stimulator is provided by receiver power supply 42, which in the preferred embodiment includes two 9 volt batteries. When timer/driver section 100 receives power it generates a plurality of 20 kHz pulses. The pulses are preferably generated, or modulated, a rate of about 10 to 120 pulses per second. This rate is referred to as the burst frequency. The 20 kHz pulse preferably have a duration of about 0.2 to 2.0 seconds. The burst frequency, duration, and duty cycle of these pulses may be adjusted. Adjustments made to these values will, in turn, affect the characteristics of the electrical stimulus pulse in a manner discussed more fully hereinafter. The 20 kHz pulses cause high current pulses to flow through the input windings of transformer 102. The low current, high voltage pulses from the high voltage output section of transformer 102 are rectified and filtered at rectifier section 104, thereby providing a modulated DC current pulses, or the electrical stimulus pulse, to electrode 6. The stimulus pulse will preferably be generated for substantially for the same length of time as the 20 kHz pulses, that is about 0.2 to 2.0 seconds, and will be at approximately the same burst frequency of those pulses. The DC electrical stimulus pulse flows from button 60, through the patient's skin, to ring 62. Current flowing back from electrode 6 flows through opto-isolator 106. Current flowing through opto-isolator 106 activates stimulation indicator means 50, thereby indicating that the stimulus has been administered to the patient.

The apparatus of this invention may be used to treat a patient as follows to deter or decelerate present undesireable behavior. Receiver/stimulator 4 and electrode 6 are preferably secured to a patient who exhibits undesired behavior, such as self-injurious behavior, for example, as described hereinbefore on reference to FIGS. 7 and 8. Referring to FIGS. 1-6, while observing the patient, a therapist may carry transmitter 2, which has been adjusted to send the appropriately coded signal corresponding to the receiver/transmitter 4 attached to the patient. When the undesired behavior is observed, the therapist may activate transmitter 2 by pressing and holding transmitter button 16, thereby generating a coded electromagnetic signal. Once the electromagnetic signal is generated, the button 16 is preferably released. Receiver/transmitter 4, upon receiving and recognizing the coded electromagnetic signal, becomes activated. In a preferred embodiment, receiver/transmitter 4 preferably does not generate an electrical stimulus pulse until the electromagnetic signal from transmitter 2 is received for a continuous period of about 0.2 to 1.0 seconds. This lessens the likelihood that an electrical stimulus pulse would be administered as a result of transmitter button 16 being accidentally pressed, such as where transmitter 2 is activated and then quickly deactivated. If transmitter 2 is continuously activated for more than about 1 to 3 seconds, a second electrical stimulus pulse will be generated and administered to the patient. The electrical stimulus pulse will be administered to the patient within about 0.2 to 1.0 seconds after receiver/stimulator 4 has been activated. As discussed hereinbefore, the current returning from electrode 6 after the stimulus has been properly administered activates stimulation indicator means 50, thereby confirming that the stimulus has been administered to the patient. Stimulation indicator means 50 will preferably remain activated while the stimulus is being administered.

Alternatively, the apparatus may be used to educate or train a patient by using a "behavior rehersal" method of treatment. With this method, a patient who is wearing the apparatus and who has exhibited undesired behavior in the past is prompted into engaging in the undesired behavior or is vividly reminded of the undesired behavior. The apparatus is activated when the patient engages in or recalls the behavior, thereby administering aversive stimulus. This type of treatment method reminds the patient that the type of undesired behavior in which he or she had engaged in the past will result in aversive stimulus being administered. Behavior rehersal is often used when the patient has exhibited undesired behavior which was extreme, such as engaging in violence against others. When this type of treatment is used, it is often desirable for the aversiveness of the stimulus, as perceived by the patient, to be less than when the stimulus is used to deter or decelerate a patient's present behavior.

Because stimulation indicator means 50 is activated by the current returning from electrode 6, it provides a positive indication that the stimulus has been administered to the patient. The stimulation indicator means of prior art devices are typically activated when the transmitter signal is received or by the generation of the stimulus pulse. Such systems do not provide a reliable indication that the stimulus has actually been administered. For example, if the electrode has been damaged or is not in electrical contact with the patient's skin, no stimulation will be administered. However, with the prior art systems, the transmitter signal will nonetheless be received and a stimulus pulse will still be generated. As a result, the stimulator indicator means of those devices will be activated and will falsely indicate that stimulus has been administered. With the present invention, if the stimulus is not administered to the patient, no current will flow back from the electrode and stimulation indicator means 50 will not be activated. This invention thereby provides feedback which positively indicates to the therapist that the stimulus has been administered.

In a preferred embodiment, stimulation indicator means 50 produces an audible signal, such as a beep. This type of signal will clearly provide the therapist with an indication that the stimulus has been administered. The audible signal produced by stimulation means 50 will preferably be loud enough to be heard over sounds made by the patient and other background noise that may be present. While a beeper has been described as a preferred embodiment for stimulation indicator means, it will be appreciated that any suitable type of stimulation indicator means may be used in lieu thereof or in addition thereto, such as visual indicator means, such as a lamp, for example, or other types of audible signals.

In a preferred embodiment, transmitter 2 will be capable of activating receiver/stimulator 4 from a distance of about 0 to 20 feet. This will enable the therapist to distance himself or herself from the patient when the stimulus is administered. This will result in a safer environment for the therapist by minimizing the need to approach the patient, thereby resulting in fewer physical confrontations between patient and therapist. This will also decrease the likelihood that the patient will come to associate the application of the stimulus pulse with the presence of the therapist. It will be appreciated that the range of the transmitter will be reduced if the patient and the therapist are separated by walls or partitions or if the patient is facing such that his or her body is disposed between the transmitter and the receiver/stimulator.

Figure 10:
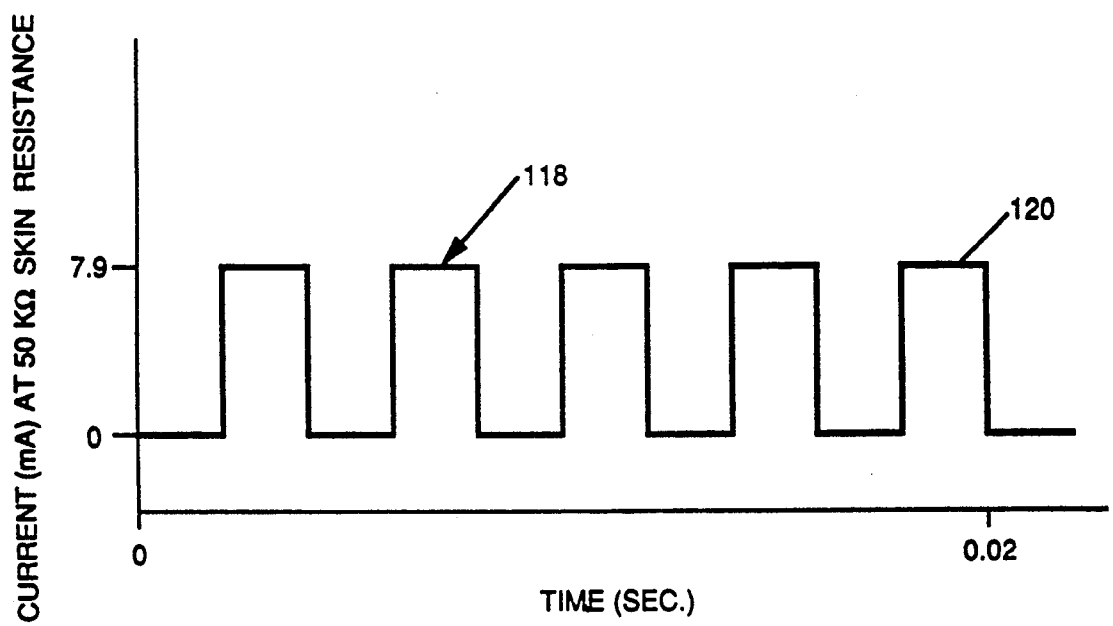
FIG. 10 is a current versus time graph of the electrical stimulus pulse generated by this invention.

Various characteristics of the electrical stimulus pulse generated by receiver/stimulator 4 may be adjusted to provide varying levels of perceived aversiveness resulting from the application of the stimulus. Referring to FIG. 10, there is shown a current versus time graph of the electrical stimulus pulse generated by the receiver/stimulator of this invention. FIG. 10 shows that the electrical stimulus pulse consists of a series of short current pulses with short periods of no current there between. This type of electrical signal is known as a rectangular waveform.

Peak current 120 of electrical stimulus pulse 118 is the maximum current of the stimulus pulse. This is one of the characteristics of the stimulus pulse that determines the perceived aversiveness of the stimulus. In general, the higher the peak current value, the greater the perceived aversiveness of the stimulus. However, a higher peak current value is more likely to result in injury to the patient's skin. Peak current value 120 may be adjusted between about 4.1 mA and 7.9 mA, based on an average skin impedance of 50 kohms. Skin that has been injured, either through repeated applications of electrical stimulus or through other means, will typically have lower impedance than uninjured skin and will, thereby, generally allow a greater peak current to flow than uninjured skin. Peak current 120 will also be affected by the condition of the receiver batteries and by the actual skin resistance of the patient.

The preferred setting for peak current value is preferably about 4.1 to 7.9 mA. This value may be adjusted using current adjusting means by varying the resistance through which the stimulus pulse must flow before reaching the electrode. In a preferred embodiment, changing the resistance is accomplished by replacing one or more resistors on the controller board. As discussed, peak current may be adjusted in order to vary the perceived adverseness of the stimulus. Accordingly, when the apparatus is being used to deter or decelerate a patient's present conduct, a high peak current value may be desired. Conversely, if the apparatus is being used with a behavior rehersal treatment, a lower peak current value may be desired. Because peak current is adjustable, the present invention may be used with both method treatments.

Duty cycle is the percentage of time during each cycle that current is flowing. This value is determined by dividing the length of time current is flowing during a cycle by the total length of time of each cycle. The duty cycle of the stimulus pulse will also affect the perceived aversiveness of the stimulus pulse. Generally, a higher duty cycle value setting will result in the perceived aversiveness of the stimulus being greater. However, a stimulus having a high duty cycle value is generally more likely to cause injury to the patient's skin than a stimulus with a lower duty cycle value since the skin will be exposed to more electrical current with higher duty cycles.

In a preferred embodiment, the duty cycle value may be adjusted between about 1% and 90%. The preferred setting for duty cycle is about 20 to 30%. Duty cycle 2 the stimulus pulse is directly related to the duty cycle of the 20 kHz pulse discussed hereinbefore. Duty cycle is preferably adjusted by using duty cycle adjusting means to change the duty cycle of the 20 kHz pulses. In a preferred embodiment, duty cycle may be adjusted by adjusting a potentiometer located in the timer/driver portion 100 of controller board 98, as shown in FIG. 9. Adjustments to the potentiometer will change the duty cycle of the 20 kHz pulses generated in timer/driver portion 100 which will, in turn, change the duty cycle of the resulting stimulus pulse.

Pulse repetition frequency is the number of pulses of peak current generated per second. Varying the pulse repetition frequency of the stimulus pulse will vary the perceived aversiveness of the stimulus to many patients. In a preferred embodiment, the pulse repetition frequency value may be adjusted between about 10 to 120 pulses per second. The preferred setting for pulse repetition frequency is about 60 to 100 pulses per second. Pulse repetition of the stimulus pulse preferably directly corresponds to the burst frequency of the 20 kHz pulses discussed hereinbefore. Pulse repetition frequency may be adjusted by using frequency adjusting means to change the burst frequency of the 20 kHz pulses. In a preferred embodiment, such adjustments are preferably made by adjusting the modulation of the 20 kHz pulses, preferably by adjusting a potentiometer on the timer/driver 100 portion of controller board 98.

Pulse train duration is the total length of time that the electrical stimulus pulse is administered to the patient. Pulse train duration has a substantial affect the perceived aversiveness of the stimulus. Generally, the longer the stimulus is administered, the greater the perceived aversiveness of the stimulus. However, a stimulus pulse having a long pulse train duration is generally more likely to cause injury to the patient's skin than is a stimulus pulse having a shorter pulse train duration. In a preferred embodiment, the pulse train duration value may be adjusted from about 0.2 to 2.0 seconds. The preferred setting for pulse train duration value is about 0.2 to 1.00 seconds.

This value may be adjusted by using duration adjusting means to vary the duration of the 20 kHz pulses generated by timer/driver 100, as discussed hereinbefore. Pulse train duration preferably corresponds directly to duration of the 20 kHz pulses. In a preferred embodiment, adjustments to pulse train duration are preferably made by adjusting potentiometer means located on the timer/driver section 100 of controller board 98, which varies to the duration of the 20 kHz pulses.

Adjusting peak current value, duty cycle value, pulse repetition frequency value and pulse train duration value allows the apparatus to be tailored to the needs of particular patients. For example, patients having injuries to the skin adjacent to the electrode may adequately respond to stimulus which is perceived only mildly averse by uninjured patients. Conversely, other patients may respond only to stimulus which is perceived as being extremely aversive to others. It has been found that the following settings result in a stimulus pulse which generally will deter or decelerate self-injurious behavior in many patients:

| Peak current: | 7.9 mA at 50 kohms skin resistance |
| --- | --- |
| Duty cycle: | 25% |
| Pulse repetition frequency: | 80 pulses per second |
| Pulse train duration: | 0.2 seconds |

The method of treatment of this invention includes securing a remotely activated apparatus for administering electrical aversive stimulus to a patient to be treated. The patient is then observed for signs of undesired behavior. If the patient is observed exhibiting such behavior, the apparatus for administering the aversive stimulus is remotely activated by the observer through the use of an electromagnetic signal thereby administering an electrical aversive stimulus pulse to the patient. The apparatus then provides positive feedback to the observer that the stimulus has been administered to the patient. If desired, the peak current value, duty cycle value, pulse repetition frequency value and pulse train duration value of the electrical aversive stimulus pulse may be adjusted in order to change the perceived aversiveness of the applied stimulus pulse.

An alternative method of treatment includes utilizing the apparatus of this invention with a behavior rehersal method of treatment, as discussed hereinbefore.

It will be appreciated that this invention provides a compact apparatus for administering electrical aversive stimulus which may be activated from a distance, and which provides a positive indication that the stimulus has been administered. Moreover, it will be appreciated that this invention provides an apparatus which generates an electrical aversive stimulus having various characteristics which may be adjusted in order to vary the perceived averseness of the stimulus. It will also be appreciated that a method of treatment using this apparatus is also provided.

For convenience of illustration, self-injurious behavior has been described as the typical type of behavior which this apparatus may be used to deter or decelerate. However, it will be appreciated by those skilled in the art that this invention may be used to deter various types of undesired behavior. It will also be appreciated that this invention may be used to educate or train individuals and animals.

Whereas particular embodiments of this invention have been described for purposes of illustration, it will be evident to those skilled in the art that numerous variations may be made without departing from the invention as defined in the appended claims.

What is claimed is:

1. Apparatus for administering electrical aversive stimulus to an individual, comprising:
   a transmitter for generating an electromagnetic signal, said transmitter having switch means for turning said signal on and off;
   a receiver/stimulator for receiving said signal from said transmitter and generating an electrical stimulus pulse in response to receiving said signal, said electrical stimulus pulse having a peak current value, a duty cycle value, a pulse repetition frequency value, and a pulse train duration value;
   an electrode electrically connected to said receiver/stimulator for transmitting said electrical stimulus pulse to the individual; and
   stimulation indicator means responsive to said electrical stimulus pulse for indicating when said electrical stimulus pulse passes from said electrode to the individual.

2. The apparatus of claim 1, wherein:
   said receiver/stimulator includes current adjusting means for adjusting said peak current value of said electrical stimulus pulse.

3. The apparatus of claim 2, wherein:
   said receiver/stimulator includes duty cycle adjusting means for adjusting said duty cycle value of said electrical stimulus pulse.

4. The apparatus of claim 3, wherein:
   said receiver/stimulator includes frequency adjusting means for adjusting said pulse repetition frequency value of said electrical stimulus pulse.

5. The apparatus of claim 4, wherein:
   said receiver/stimulator includes duration adjusting means for adjusting said pulse train duration value of said electrical stimulus pulse.

6. The apparatus of claim 5, wherein:
   said stimulation indicator means includes means for generating an audible signal.

7. The apparatus of claim 6, wherein:
   cord means electrically connect said electrode to said receiver/stimulator, whereby said electrode is positionable in a location that is remote from said receiver/stimulator.

8. The apparatus of claim 7, further comprising:
   harness means for holding said electrode in electrical contact with the individual.

9. The apparatus of claim 8, wherein:
   said transmitter has coding means for coding said electromagnetic signal; and
   said receiver/stimulator has decoding means for recognizing said coded electromagnetic signal, whereby said electrical stimulus pulse is generated only in response to a recognized electromagnetic signal.

10. The apparatus of claim 9, wherein:
    said electrode has a button portion disposed within a ring portion.

11. The apparatus of claim 10, wherein:
    said receiver/stimulator has current adjusting means for adjusting said peak current value of said electrical stimulus between about 4.1 and 7.9 mA based on a skin impedance of about 45 to 55 Kohms.

12. The apparatus of claim 11, wherein:
    said receiver/stimulator has duty cycle adjusting means for adjusting said duty cycle value of said electrical stimulation pulse between about 1 to 90%.

13. The apparatus of claim 12, wherein:
said receiver/stimulator has frequency adjusting means for adjusting said pulse repetition frequency value said electrical stimulus pulse between about 10 to 120 pulses per second.

14. The apparatus of claim 13, wherein:
said receiver/stimulator has duration adjusting means for adjusting said pulse train duration value of said electrical stimulus pulse between about 0.2 to 2.0 seconds.

15. The apparatus of claim 14, wherein:
said button portion of said electrode is about 0.35 to 0.40 inches in diameter; and
said ring portion of said electrode has an inner diameter of about 0.52 and 0.60 inches, an outer diameter of about 0.85 to 0.90 inches, and about 0.25 to 0.38 inches between an inner perimeter and an outer perimeter of said ring portion.

16. A method of treating an individual using electrical aversive stimulus, comprising the steps of:
securing to an individual a remotely controlled apparatus for administering electrical aversive stimulus, said apparatus having a receiver/stimulator and an electrode electrically connected to said receiver/stimulator;
securing said electrode in electrical contact with said individual;
observing said individual for undesired behavior;
remotely activating said apparatus when undesired behavior is observed, such that electrical aversive stimulus is administered to said individual, said electrical aversive stimulus having desired peak current value, duty cycle value, pulse repetition frequency value, and pulse train duration value; and
monitoring stimulus feedback from said apparatus which indicates that said electrical aversive stimulus has been administered to said individual.

17. The method of claim 16, including:
adjusting said peak current value of said electrical aversive stimulus to alter the perceived aversiveness of said stimulus.

18. The method of claim 17, including:
adjusting said duty cycle value of said electrical aversive stimulus to alter the perceived aversiveness of said stimulus.

19. The method of claim 18, including:
adjusting said pulse repetition frequency value of said electrical aversive stimulus to alter the perceived aversiveness of said stimulus.

20. The method of claim 19, including:
adjusting said pulse train duration value of said electrical aversive stimulus pulse to alter the perceived aversiveness of said stimulus.

21. The method of claim 19, further including the step of:
maintaining said peak current value between about 4.1 and 7.9 mA based on a skin impedance of about 45 to 55 Kohms.

22. The method of claim 21, including:
maintaining said duty cycle value between about 1 to 90%.

23. The method of claim 22, including:
maintaining said pulse repetition frequency value between about 10 to 120 pulses per second.

24. The method of claim 23, including:
maintaining said pulse train duration value between about 0.2 to 2.0 seconds.

25. The method of claim 24, including:
remotely activating said apparatus using a remotely generated electromagnetic signal.

26. The method of claim 25, further including the steps of:
securing said receiver/stimulator to the torso of said individual using a harness having at least one shoulder strap and at least one belt; and
securing said electrode to a limb of said individual using an electrode harness.

27. The method of claim 26, including:
employing said method an individual who is a patient.

28. A method of treating an individual using electrical aversive stimulus, comprising the steps of:
securing to an individual a remotely controlled apparatus for administering electrical aversive stimulus, said apparatus including a receiver/stimulator and an electrode electrically connected to said receiver/stimulator;
securing said electrode in electrical contact with said individual;
prompting said individual to engage in undesired behavior;
remotely activating said apparatus when said individual engages in said undesired behavior, such that electrical aversive stimulus is administered to said individual, said electrical aversive stimulus having desired peak current value, duty cycle value, pulse repetition frequency value, and pulse train duration value; and
monitoring stimulus feedback from said apparatus which indicates that said electrical aversive stimulus has been administered to said individual.

29. The method of claim 28, including:
adjusting said peak current value of said electrical aversive stimulus to alter the perceived aversiveness of said stimulus.

30. The method of claim 29, including:
adjusting said duty cycle value of said electrical aversive stimulus to alter the perceived aversiveness of said stimulus.

31. The method of claim 30, including
adjusting said pulse repetition frequency value of said electrical aversive stimulus to alter the perceived aversiveness of said stimulus.

32. The method of claim 31, including:
adjusting said pulse train duration value of said electrical aversive stimulus pulse to alter the perceived aversiveness of said stimulus.

* * * * *

UNITED STATES PATENT AND TRADEMARK OFFICE
CERTIFICATE OF CORRECTION

PATENT NO. : 5,304,211
DATED : April 19, 1994
INVENTOR(S) : Matthew L. Israel and David Marsh It is certified that error appears in the above-identified patent and that said Letters Patent is hereby corrected as shown below:

Column 2, line 61, -- administer -- should be inserted after the second occurrence of "to".

Column 2, line 62, "administer" should be deleted.

Signed and Sealed this

Eleventh Day of July, 1995

Attest:

BRUCE LEHMAN

Attesting Officer

Commissioner of Patents and Trademarks